US008821947B2

(12) United States Patent
Selby, III

(10) Patent No.: US 8,821,947 B2
(45) Date of Patent: Sep. 2, 2014

(54) CHOLESTEROL-REDUCING DIET

(76) Inventor: Howard W. Selby, III, Boulder, CO (US)

(*) Notice: Subject to any disclaimer, the term of this patent is extended or adjusted under 35 U.S.C. 154(b) by 1502 days.

(21) Appl. No.: 11/798,186

(22) Filed: May 10, 2007

(65) Prior Publication Data

US 2008/0070826 A1    Mar. 20, 2008

Related U.S. Application Data

(60) Provisional application No. 60/809,852, filed on Jun. 1, 2006.

(51) Int. Cl.
*A61K 36/00* (2006.01)

(52) U.S. Cl.
CPC ..................................... *A61K 36/00* (2013.01)
USPC ............................................ 424/725; 434/127

(58) Field of Classification Search
None
See application file for complete search history.

(56) References Cited

U.S. PATENT DOCUMENTS

| 6,610,320 | B2 | 8/2003 | Schmitz |
| 6,995,189 | B1 | 2/2006 | Turini |

FOREIGN PATENT DOCUMENTS

| WO | WO 01/19356 | * | 3/2001 |

OTHER PUBLICATIONS

Agatston (The South Beach Diet. 2003. Rodale: USA, pp. 10-12, 32-38, 70, 126, and 127).*
Lopez (Archives of Medical Research (1996), vol. 27, No. 4, pp. 519-523).*
http://en.wikipedia.org/wiki/Glycemic_index—accessed Apr. 2014.*
Lara-Castro et al, "Diet, Insulin Resistance and Obesity: Zoning on on Data For Atkins Dieters Living in South Beach", J. Clinical Endocrinology and Metabolism, (2004), v. 89, No. 9, pp. 4197-4205.
Agatston, "The South Beach Diet" (2003), p. 70.
Brown et al, "Lowering LDL—Not only How Low, but How Long?", Science, vol. 311 (Mar. 24, 2006), pp. 1721-1723.
Grundy, et al,"Diagnosis and Management of the Metabolic Syndrome", Circulation (2005).
Nissen, "Effect of intensive lipid lowering on progression of coronary atherosclerosis" Am. J. Cardiol. (2005) (abstract only).
Nawrocki et al, Reduction of LDL Cholesterol by 25% to 60% in Patients . . . Arteriosclerosis, Thrombosis and Vascular Biology (1995) 15, 678-682.
Grundy et al,"Implications of Recent Clinical Trials for the National Cholesterol Education Program Adult Treatment Panel III Guidelines",(2004).

* cited by examiner

*Primary Examiner* — Susan Hoffman
(74) *Attorney, Agent, or Firm* — Michael de Angeli

(57) ABSTRACT

A method of treating cholesterol imbalance, high LDLs, and other metabolic syndrome problems and symptoms of osteoarthritis. The regimen preferred embodiment includes lipids as 60% or more of daily caloric content, protein up to 10%-15% of daily caloric content; and carbohydrates up to 25% or less of daily caloric content, primarily in the form of non-starchy, low-glycemic fresh fruit and vegetables, and nuts, along with a daily intake of 35 grams of dietary fiber, with a significant percentage of this as soluble fiber; average daily cholesterol intake of less than 10 mg, and 30 grams of cocoa solids.

2 Claims, No Drawings

CHOLESTEROL-REDUCING DIET

CROSS-REFERENCE TO RELATED APPLICATION

This application claims priority from Provisional Application Ser. No. 60/809,852, filed Jun. 1, 2006.

BACKGROUND OF THE INVENTION

Atherosclerotic cardiovascular disease (ASCVD) is the most prevalent health problem in the developed world. The incidence of ASCVD has grown at an alarming rate due to shifts in people's lifestyles. These shifts are primarily changes in diet, but also include decreases in physical activity and increases in stress levels. They have been accompanied by a rising onset of adult diabetes and body weight gain. This condition is now being referred to as metabolic syndrome.

According to the Executive Summary of the 18 Oct. 2005 article, "Diagnosis and Management of the Metabolic Syndrome, An American Heart Association/National Heart, Lung, and Blood Institute Scientific Statement":

"This Executive Summary is a synopsis of the full scientific statement from the American Heart Association (AHA) and the National Heart, Lung, and Blood Institute (NHLBI), which is intended to provide up to date guidance for professionals on the diagnosis and management of the metabolic syndrome in adults.

The metabolic syndrome has received increased attention in the past few years. It consists of multiple, interrelated risk factors of metabolic origin that appear to directly promote the development of atherosclerotic cardiovascular disease (ASCVD). This constellation of metabolic risk factors is strongly associated with type 2 diabetes mellitus or the risk for this condition. The metabolic risk factors consist of atherogenic dyslipidemia (elevated triglycerides and apolipoprotein B, small LDL particles, and low HDL cholesterol [HDL-C] concentrations), elevated blood pressure, elevated plasma glucose, a prothrombotic state, and a proinflammatory state."

(For more details, see complete report of the same title of the same date.)

The most significant indicator of ASCVD and coronary risk is hypercholesterolemia or a high cholesterol level. Originally, tests simply tested total cholesterol, but now more sophisticated tests called lipid or cholesterol panels measure the separate components of cholesterol: low density lipoproteins or "LDLs" (known as the undesirable, or "bad" cholesterol), high density lipoproteins or "HDLs" (the desirable, or "good" cholesterol), very low density lipoproteins or "VLDLs", and triglycerides. Both the LDL to HDL ratio and LDLs alone are used to compute coronary heart disease risk factors.

The causal relationship is well established with the higher the LDL level or LDL:HDL ratio, the greater the risk of coronary heart disease. The Adult Treatment Panel III (ATP III) of the National Cholesterol Education Program issued an evidence-based set of guidelines in 2001, and then in 2004 published an update in Circulation labeled "Implications of Recent Clinical Trials for the National Cholesterol Education Program. Adult Treatment Panel III Guidelines." The improvements and knowledge gained in the five major clinical trials discussed in the latter paper provide valuable background into the understanding of the utility of the present invention.

The most-prescribed drugs in America are statins (HMG-CoA reductase inhibitors), which are drugs to help reduce high LDL-levels. The present invention is as effective as statins in reducing the LDL ("bad cholesterol") levels, and, unlike statins, it also increases the HDL ("good cholesterol") levels and reduces the triglyceride levels. In Table 1 of the AHA/NHLBI document cited above, low HDLs and high triglycerides are now earmarked as two of the diagnostic criteria for the indication of metabolic syndrome. Concerning LDL reduction, both statins and the present invention reduce the LDL number in a standard lipid panel (the standard lipid panel does not differentiate between large and small particle LDLs). However, there is a significant difference in the nature and mechanism of the LDL reduction of statins and the present invention. Statins primarily reduce the large particle LDLs, while the present invention primarily reduces the more problematic small particle LDLs (see "Executive Summary" referenced above).

The present invention also appears to be useful in alleviating symptoms of other related diseases. More specifically, the ability of the invention to markedly reduce or eliminate symptoms of osteoarthritis and seasonal allergies in participants who have had these problems has been demonstrated. The fact that the regime of the invention reduces arterial stiffness may have beneficial effects on other health concerns as well. Specifically, it appears that Alzheimer's disease and dementia can be caused at least in part by "micro-strokes". Arterial stiffness can lead to stroke. The invention may also be useful in reducing these conditions.

This invention achieves these significant changes without the use of pharmacological agents, but rather through the use of a specific nutritional regimen (described more specifically below) which shifts the subject's mode of metabolism.

SUMMARY OF THE INVENTION

The present invention is the use of a lipid-dominant approach to diet which shifts the body's metabolism to reduce and balance cholesterol levels and treat metabolic syndrome. Specifically, the invention is a complete and specific nutrition regimen with key parameters which result in a rapid reduction of high LDL levels, as well as a reduction in triglycerides and an increase in HDL levels, when the triglycerides and HDL levels are out of balance.

The uniqueness of the invention is that it accomplishes these results through diet, requiring only everyday, commonplace foods, and no pharmaceuticals. Furthermore, it adjusts the key cholesterol components—LDLs, HDLs, VLDLs, and triglycerides—as quickly and more effectively than by the use of statin drugs, which affect only LDLs and generally do not affect HDLs, VLDLs or triglycerides.

The speed and efficacy of the invention is remarkable (see the Pilot Participants Chart appended hereto as Appendix A). In just two weeks, users of the invention achieve results equivalent to those produced by high-dosage regimens of statin drugs. Most cases of hypercholesterolemia are brought into balance within a two-week period; severe cases may take slightly longer.

A key aspect of the invention is that the subject's caloric daily intake is lipid-dominant (e.g., 50% or more of total). Nutrients required for maintenance of health. (primarily vitamins, minerals, protein, carbohydrates, and essential fatty acids), are selected to complement and enhance the action of this lipid component. Without limiting the invention, it is believed at present that this approach is effective in reducing LDLs because the high levels of lipids in the diet cause the body to operate dominantly in lipid-energy metabolic mode. This mode causes residual serum LDLs to be metabolized or removed. The process thereby allows the body to manufacture and maintain only the amount of LDL cholesterol it needs in order to properly function. In turn, it allows the body to regain its natural balance in overall metabolic function.

This invention runs counter to the current medical recommendations of low-fat diets to treat ASCVD. The American Heart Association and the National Heart, Lung, and Blood Institute, in the document cited above, advocate an atherogenic diet which recommends a 25%-35% lipid content. At the other end of the spectrum, Dr. Dean Ornish, who has done extensive work in the area of reversing ASCVD, prescribes a 10% lipid content diet in his book, Dr. Dean Ornish's *Program for Reversing Heart Disease.*

Neither of these plans—or any other—achieve either the high-speed cholesterol reduction or the important cholesterol balancing of this invention. The results of the invention's Pilot Participants showed 100% of participants reducing their LDL cholesterol counts by an average of 50 mg/dl within the two-week period, and even as much as 10 mg/dl within a few days. The Pilot Participants moreover showed balancing where needed, pulling up the HDLs and reducing the triglycerides.

The invention also solves the ever-present hunger and low compliance problems associated with high-carbohydrate, low-fat diets. Due to the high lipid content of this invention, users do not experience ravenous hunger pangs, but instead find it easier to feel satisfied. In addition, users of this invention are able to see extensive, measurable results, which are obtained in very short amounts of time. Normally users have experienced an LDL level drop of 30-40% in two weeks and a weight loss of five pounds a week. This quick and quantifiable feedback, combined with the lack of hunger sensations and the short two-week length of the program, results in motivated subjects and high compliance.

The invention may be used for an extended period longer than the two weeks to attain further weight loss (incidentally, abdominal obesity is another of the AHA/NHLBI diagnostic criteria mentioned earlier for metabolic syndrome). By simply increasing lipid intake, the invention can also be used for weight gain if that is what the individual needs.

It is also anticipated that the continued use of the invention for treatment of ASCVD will not simply halt but actually reverse arterial sclerosis. A article in the *American Journal of Cardiology on* 5 Sep. 2005, "Effect of Intensive Lipid Lowering on Progression of Coronary Atherosclerosis: Evidence for an Early Benefit from the Reversal of Atherosclerosis with Aggressive Lipid Lowering (REVERSAL) Trial," as well as an article in Science on 24 Mar. 2006, "Lowering LDL—Not Only How Low, but How Long?", discuss how very low LDL levels lead to the reversal of arterial sclerosis. These articles reference the use of statins to reduce LDL counts. As discussed, the invention's diet, without the use of drugs, achieves these same low LDL levels. Participants using the invention show continual reduction in vascular stiffness, thereby indicating that vascular health is being improved.

It is also within the invention to combine the diet with a regimen of small dosages of statins to reach even lower LDL levels. The mechanisms of action of the diet of the invention and of statins are different, so the combination works in a complementary fashion to attain extremely low LDL levels. This form of the invention can therefore be employed to aggressively accelerate the reversal of arterial sclerosis.

As has been shown, the invention promotes a systemic balancing within the body. In this way, it can be used for not only quick results, but also for long-term maintenance of lowered, balanced levels of cholesterol. It is an overall solution for treating metabolic syndrome.

PREFERRED EMBODIMENT OF THE INVENTION

The diet according to this invention generally involves at least a two-week initial regimen, during which users follow specific guidelines regarding their food intake. Users are encouraged to eat frequently; generally, this will result in a daily schedule of three main meals, and four snacks. Additional snacks are permitted as well, within the diet guidelines.

Basic diet guidelines for the preferred embodiment are as follows:
1. Lipids comprise at least 50% and preferably 60% or more of daily caloric content, of which 50% are monosaturated fats;
2. Daily intake of 35 grams of dietary fiber (with a significant percentage of this as soluble fiber);
3. Average daily cholesterol intake of less than 10 mg;
4. Minimal intake of saturated fats (generally less than 15 grams/day);
5. Daily intake of 30 grams of cocoa solids;
6. Protein comprises 10%-15% of daily caloric content; and
7. Carbohydrates are limited, comprising 25% or less of daily caloric content (primarily non-starchy, low-glycemic fresh fruit and vegetables, and nuts).

As described above, the diet is lipid-centric. Instead of the diet observed by most Americans, in which the majority of calories are derived from carbohydrate sources, in this diet the majority of the user's calories come from lipid sources. Specifically, at least 50% (60% or more in the preferred embodiment) of the user's daily caloric intake is in the form of lipids (preferably olive, canola, or flax oil, and also including avocados and some nuts). Of these lipid calories, 50% or more are comprised of monounsaturated fats.

The primary source of these lipids, in the preferred embodiment, is olive oil. (However, other lipid sources may be used.) The user eats 60-110 grams of olive oil each day. (The specific gram amount will depend on several factors, including the total daily caloric intake, and whether the user wishes to gain, lose, or maintain his or her overall body weight.) Other sources of lipids are tofu, walnuts, other nuts and seeds, and fish oil (which additionally provides important omega-3 fatty acids). Generally, the user takes the fish oil in the form of capsule supplements.

The diet regimen includes the minimum necessary amount of protein, and a restricted amount of low-glycemic-index carbohydrates.

Protein comprises between 10% and 15% of the user's daily caloric intake. Generally, the user has a target protein intake target of 30-50 grams per day. (Again, this may vary based on overall caloric intake levels and activity level.) The principal source of protein used is egg whites. The two other protein sources included in the diet are tofu, and non-fat, non-cholesterol strained yogurt. No cholesterol-containing dairy products are eaten during the two-week period.

Carbohydrate intake is restricted in quantity during the diet, comprising 25% or less of the daily caloric intake, and is made up only of foods with a low glycemic index. Legumes, beans, cereals, rice, bread, pasta, and grains are not eaten during the two-week cholesterol reducing and balancing period. Almost all of the carbohydrates consumed are from vegetables and fruits. Only vegetables and fruits with a low glycemic index are used. Starchy vegetables such as potatoes, corn, and carrots are not eaten.

Vegetables are eaten both cooked and raw. Large salads, made up of a variety of mixed greens, and augmented with vegetables such as fennel, peppers, and tomatoes, are the mainstay of each day's lunch and dinner. It is recommended that the user adds vegetables to the egg whites each morning, for nutrients and flavor.

These vegetables are also instrumental in providing the user with dietary fiber, poly phenols and antioxidants. A minimum of 35 grams of dietary fiber are eaten each day. The fiber naturally found in vegetables is augmented by the user's taking psyllium husk fiber supplements twice daily, immediately upon rising in the morning, and directly before going to bed in the evening.

The above preferred embodiment is additionally complemented by users eating 30 grams of natural, unsweetened, non-Dutch cocoa powder every day. Cocoa has demonstrated its ability to reduce cardiac risk in numerous studies and so has been added to the diet and for its popularity. A recommended method of eating the cocoa powder is in the form of two hot cocoa drinks, each of which is made by mixing 15 grams of unsweetened cocoa powder with up to six ounces of low-sugar almond milk.

During the two-week diet, the user will drink about 48 ounces of water and/or tea each day. Coffee and wine are permitted, but only in moderation. Fruit juice and sweetened drinks, including soda pop, are not a part of the regimen nor is milk.

Seasonings such as salt, pepper, spices and herbs, garlic, ginger, lime and lemon juice, and hot sauces are allowed and encouraged for flavor. However, the user does not eat any starchy or sweetened sauces or dressings.

During the diet, the user continues with any vitamins or supplements he or she regularly takes. The user's doctor would advise as to any other medications or prescribed medications.

It is also within the invention to combine the diet as described above along with a regimen of statin drugs. The two mechanisms complement each other to achieve extremely low LDL levels. Thus, when more aggressive treatment is indicated, the invention in the form of a combination of diet and low level doses of statins can provide more rapid reversal of coronary disease and treatment of metabolic syndrome.

APPENDIX A

Pilot Participants: High-Speed Cholesterol Reduction and Balancing Regime

PRE-DIET BASELINE

| | Age | Statins | BL Start Weight | BL Start BMI | BL Lipid Profile Test Date | Total Chol | Tri-glyc | HDL | LDL | VLDL | LDL/HDL RISK |
|---|---|---|---|---|---|---|---|---|---|---|---|
| 1 | 64 | N | 162.0 | 23.9 | Jan. 24, 2006 | 219 | 91 | 84 | 117 | 18 | 0.6 |
| 2a | 69 | N | 159.5 | 24.2 | Jan. 28, 2005 | 170 | 47 | 42 | 119 | 9 | 1.0 |
| 2b | 69 | N | 159.5 | 24.2 | Feb. 24, 2006 | 180 | 48 | 56 | 115 | 9 | 0.8 |
| 3 | 54 | N | 109.0 | 19.0 | Jan. 24, 2006 | 266 | 75 | 80 | 171 | 15 | 0.8 |
| 4 | 61 | Lipitor 10 mg | 213.8 | 30.7 | Apr. 18, 2006 | 199 | 191 | 46 | 115 | 38 | 1.0 |
| 5 | 65 | N | * | * | May 1, 2006 | 290 | 156 | 74 | 185 | 31 | 0.8 |
| 6 | 67 | N | * | * | Apr. 24, 2006 | 220 | * | 63 | 142 | * | * |
| 7 | 56 | N | 136.9 | 23.1 | Apr. 28, 2006 | 229 | 82 | 64 | 149 | 16 | 0.8 |
| 8 | 58 | Lipitor 10 mg | 170.0 | 24.7 | May 2, 2006 | 170 | 81 | 56 | 98 | 16 | 0.8 |
| 9 | 28 | N | 121.0 | 21.8 | May 9, 2006 | 202 | 82 | 69 | 117 | 16 | 0.6 |

DIET PHASE

| | Length of DP | DP Start Weight | DP Start BMI | DP Lipid Profile Test Date | Total Chol | Tri-glyc | HDL | LDL | VLDL | LDL/HDL RISK | DP End Weight | DP End BMI |
|---|---|---|---|---|---|---|---|---|---|---|---|---|
| 1 | 14 days | 162.0 | 23.9 | Feb. 10, 2006 | 191 | 69 | 103 | 75 | 13 | 0.4 | 160.0 | 23.6 |
| 2a | 14 days | 159.5 | 24.2 | Feb. 24, 2006 | 180 | 48 | 56 | 115 | 9 | 0.8 | 159.5 | 24.2 |
| 2b | 20 days | 159.6 | 24.3 | Apr. 27, 2006 | 159 | 50 | 60 | 89 | 10 | 0.6 | 155.2 | 23.6 |
| 3 | 14 days | 109.0 | 19.0 | Mar. 3, 2006 | 210 | 69 | 76 | 121 | 13 | 0.6 | 107.0 | 18.7 |
| 4 | 16 days | 213.7 | 30.7 | May 17, 2006 | 144 | 159 | 53 | 60 | 31 | 0.6 | 206.0 | 29.6 |
| 5 | 4 days | * | * | May 8, 2006 | 268 | 70 | 78 | 176 | 14 | 0.8 | * | * |
| 6 | 14 days | 119.3 | 19.1 | May 18, 2006 | 160 | 76 | 55 | 90 | 15 | 0.6 | 119.9 | 19.2 |
| 7 | 6 days | 135.4 | 22.9 | May 14, 2006 | 192 | 69 | 73 | 106 | 13 | 0.5 | 133.0 | 22.5 |
| 8 | 14 days | 173.0 | 25.5 | May 26, 2006 | 127 | 58 | 68 | 48 | 11 | 0.4 | 165.7 | 24.5 |
| 9 | 16 days | 121.0 | 21.8 | May 30, 2006 | 151 | 72 | 64 | 73 | 14 | 0.5 | 119.4 | 21.5 |

CHANGE

| | Weight (lbs) | BMI | Total Chol | Tri-glyc | HDLs | LDLs | VLDL | LDL/HDL RISK | COMMENTS |
|---|---|---|---|---|---|---|---|---|---|
| 1 | −2.0 | −0.3 | −28 | −22 | 19 | −42 | −5 | −0.2 | 100% compliance |
| 2a | 0.0 | 0.0 | 10 | 1 | 14 | −4 | 0 | −0.2 | NOTE: This test was not using the full diet. Participant used only one element of the diet - focusing on increasing HDL levels. |
| 2b | −4.4 | −0.7 | −21 | 2 | 4 | −26 | 1 | −0.2 | NOTE: This test involved the same participant as 2a. This test used the full diet. Participant had 80% compliance. |
| 3 | −2.0 | −0.3 | −56 | −6 | −4 | −50 | −2 | −0.2 | 1st 6 days: Poor compliance 2nd 8 days: 95% compliance |
| 4 | −7.7 | −1.1 | −55 | −32 | 7 | −55 | −7 | −0.4 | |
| 5 | * | * | −22 | −86 | 4 | −9 | −17 | 0.0 | |
| 6 | 0.6 | 0.1 | −60 | * | −8 | −52 | * | * | NOTE: Diet duration only 4 days. |
| 7 | −2.4 | −0.4 | −37 | −13 | 9 | −43 | −3 | −0.3 | NOTE: Diet duration only 6 days. |
| 8 | −7.3 | −1.0 | −43 | −23 | 12 | −50 | −5 | −0.4 | |
| 9 | −1.6 | −0.3 | −51 | −10 | −5 | −44 | −2 | −0.1 | |

* data to be added

What is claimed is:

1. A method of treating hypercholesterolemia to be followed as a continuing lifelong regimen, said method comprising the step of limiting all food intake such that approximately 70% of daily calories are provided as lipids, carbohydrate intake is limited to no more than 25% of daily calories provided in the form of at least 200 grams of non-starchy, low-glycemic vegetables and fruit, foods having high glycemic index or high glycemic load are excluded, all grains are excluded, and essential vitamins, minerals, and fatty acids, and the minimum amount of protein that will provide for a particular individual's protein requirement are included.

2. The method of claim 1, wherein the daily calorie content includes approximately 30 grams of cacao solids as dark chocolate or unsweetened cocoa.

* * * * *